(12) United States Patent
Ho (10) Patent No.: US 7,324,203 B2
(45) Date of Patent: Jan. 29, 2008

(54) METHOD AND APPARATUS FOR OPTICAL DETECTION FOR MULTI-PHASE COMBUSTION SYSTEMS

(75) Inventor: Chi Ming Ho, Medina, OH (US)

(73) Assignee: General Electric Company, Schenectady, NY (US)

( * ) Notice: Subject to any disclaimer, the term of this patent is extended or adjusted under 35 U.S.C. 154(b) by 404 days.

(21) Appl. No.: 10/906,196

(22) Filed: Feb. 8, 2005

(65) Prior Publication Data

US 2006/0176486 A1 Aug. 10, 2006

(51) Int. Cl.
*G01N 21/00* (2006.01)

(52) U.S. Cl. ............... 356/437; 356/432; 356/440; 422/82.09

(58) Field of Classification Search ........ 356/432–439, 356/440, 442; 436/167; 422/82.09
See application file for complete search history.

(56) References Cited

U.S. PATENT DOCUMENTS

| | | | | |
|---|---|---|---|---|
| 4,010,048 A | | 3/1977 | Tesk et al. ............ | 148/24 |
| 5,007,740 A | * | 4/1991 | Jeannotte et al. ........ | 356/436 |
| 5,252,060 A | * | 10/1993 | McKinnon et al. ....... | 356/435 |
| 2005/0009081 A1 | | 1/2005 | McFarland et al. ....... | 435/6 |

FOREIGN PATENT DOCUMENTS

| WO | WO01/33200 | 5/2001 |
|---|---|---|
| WO | WO2004090496 | 10/2004 |

OTHER PUBLICATIONS

EP Search Report—EP 06250486.

Arnold, A., et al. "Laser in situ monitoring of combustion processes" Applied Optics, Optical Society of America, New York, US; vol. 29, No. 33, Nov. 20, 1990. pp. 4860-4872.

McAleavey, Fergal J., et al.; "Narrow Linewidth, Tunable $Tm^{3+}$—Doped Fluoride Fiber Laser for Optical-Based Hydrocarbon Gas Sensing" IEEE Journal of Selected Topics in Quantum Electronics; vol. 3, No. 4, Aug. 1997. pp. 1103-1111.

Teichert, Holger, et al. "Simulataneous in situ measurement of CO, $H_2O$, and gas temperatures in a full-sized coal-fired power plant by near-infrared diode lasers" Applied Optics; vol. 42, No. 12, Apr. 20, 2003. pp. 2043-2051.

Upschulte, Bernard L., et al. "Measurements fo CO, $CO_2$, and $H_2O$ in room-temperature and combustion gases by use of a broadly current-tuned multisection InGaAsP diode laser" Applied Optics; vol. 38, No. 9, Mar. 20, 1999. pp. 1506-1512.

* cited by examiner

*Primary Examiner*—Gregory J. Toatley, Jr.
*Assistant Examiner*—Iyabo S Alli
(74) *Attorney, Agent, or Firm*—Cantor Colburn LLP

(57) ABSTRACT

A method for in-situ monitoring of an emission product includes transmitting a light, tuning the light to a first wavelength, receiving the light at a second location, varying the light from the first wavelength to a second wavelength during a first period, measuring a first absorption line and a first non-absorbing baseline signal during the first period, switching the light to a third wavelength, varying the light from the third wavelength to a fourth wavelength over a second period, and measuring a second absorption line and a second non-absorbing baseline signal during the second period. The light is transmitted from a first location by a tunable light source and received at a second location. The light passes along an optical path through the emission product between the first and second locations. The first wavelength corresponds to the first absorption line of the emission product. The third wavelength is different from the first and second wavelengths.

20 Claims, 6 Drawing Sheets

METHOD AND APPARATUS FOR OPTICAL DETECTION FOR MULTI-PHASE COMBUSTION SYSTEMS

BACKGROUND OF THE INVENTION

The present invention relates to an optical detection system and, more particularly, to an optical detection system for use in a multi-phase flow combustion system.

There is a recent trend toward improving the operation of industrial process plants in the areas of efficiency, emissions, reliability, and safety. Sensor technology is becoming more important than ever for achievement of success in the above mentioned areas. High quality sensor data obtained from real-time, in-situ, and spatially resolved measurements are critical for on-line or off-line optimization, emissions monitoring, system or component health monitoring, and detecting warning signs of impending catastrophic failures.

A sampling system that performs conventional extractive types of measurements provides quasi in-situ, and spatially resolved data, but cannot provide real-time data due to an inherent delay associated with the sampling system. Furthermore, once a sample gas is extracted, it follows a different flow path and its original properties may be modified. Therefore, for high quality sensor data, a conventional extractive type sampling system is not appropriate and another type of sensor is sought.

For many industrial processes, the multi-phase flow combustion system, a coal-fired furnace for example, presents extremely harsh environments for the application of sensor technology. Very few sensors can survive the high temperature, for example, inside a flame zone of the coal-fired furnace. Those sensors that survive are often either prohibitively expensive, require high maintenance, or have a limited life. For a multi-phase flow combustion system such as the coal-fired furnace, intrusive sensors for in-situ measurements encounter even more challenging problems. Particulates can adhere to surfaces of the sensor and plug up a probe. A reducing or oxidizing environment can also cause unwanted reactions on the surfaces of the sensor leading to sensor failures.

Optical sensors have been employed in non-intrusive gas sensing to avoid the problems mentioned above. Optical sensing techniques generally involve either detection of light emitted from the multi-phase flow or detection of the response of the multi-phase flow as it interacts with an external light source. When employed in a large-scale reaction type multi-phase flow, optical sensors are also susceptible to practical problems. Particles in the multi-phase flow can severely block or scatter light. Broadband absorption by molecules such as H2O can greatly attenuate the light. The limited intensity of the probing light beam may not fully penetrate a multi-phase flow field, particularly if the multi-phase flow field is large, the particulate loading is high, or the concentration of a species capable of broadband absorption is high. Similarly, light emissions from the far side of the line-of-sight may be blocked, scattered, or absorbed before the light emissions can reach the detector. Particles often foul the optical surfaces. Other problems common to multi-phase flow, which is turbulent and has non-uniform thermal and chemical properties, are beam steering and the inability of de-convoluting spatial variations along the line-of-sight.

Sensors are often dedicated to only one type of measurement. Thus, multiple detection systems including different types of sensors are required to meet multiple sensing needs. A cost and complexity of installing multiple detection systems is a hindrance to broad application of multiple detection systems. Sensors that can perform more than one type of measurement are limited, but are definitely attractive in terms of cost and simplicity.

Multiple location sensing is desirable for determining spatial variations, and capturing different phenomena that take place in different locations of the reactive type multi-phase flow. This requires multiple sensors. In some cases, it may even require different kinds of sensors. The cost of the system is usually proportional to the number of sensors installed.

Given the problems discussed above, it is desirable to design components capable of integrating multiple measurement types in one sensor. It is also desirable to provide cost effective methods for sensing at multiple locations of a widely changing operating environment, locations starting from the burners and ending at the exhaust stack.

BRIEF DESCRIPTION OF THE INVENTION

Exemplary embodiments of the invention include a method for in-situ monitoring of an emission product. The method includes transmitting a light, tuning the light to a first wavelength, receiving the light at a second location, varying the light from the first wavelength to a second wavelength during a first period, measuring a first absorption line and a first non-absorbing baseline signal during the first period, switching the light to a third wavelength, varying the light from the third wavelength to a fourth wavelength over a second period, and measuring a second absorption line and a second non-absorbing baseline signal during the second period. The light is transmitted from a first location by a tunable light source and received at a second location. The light passes along an optical path through the emission product between the first and second locations. The first wavelength corresponds to a first absorption line of the emission product. The third wavelength is different from the first and second wavelengths.

Further exemplary embodiments of the invention include a spectrographic sensing system for in-situ monitoring of an emission product. The system includes a tunable light source, a detector, and an optical network. The tunable light source is capable of tuning a laser beam over a range of about 80 nm at a tuning rate of $10^6$ nm/sec. The detector is configured to receive the laser beam. The optical network is disposed in a flow field. The optical network provides optical communication between the tunable light source and the detector.

The above, and other objects, features and advantages of the present invention will become apparent from the following description read in conjunction with the accompanying drawings, in which like reference numerals designate the same elements.

BRIEF DESCRIPTION OF THE DRAWINGS

Referring now to the drawings wherein like elements are numbered alike in the several FIGURES.

DETAILED DESCRIPTION OF THE INVENTION

Figure 1:
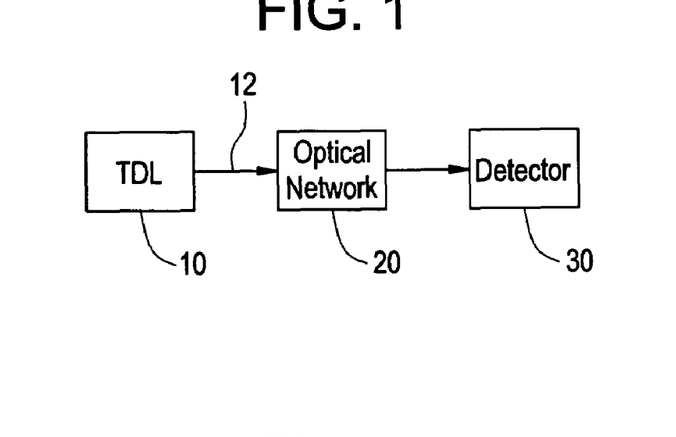
FIG. 1 is a block diagram of an optical detection system according to an exemplary embodiment.

FIG. 1 shows a block diagram of an optical detection system suitable for performing spatially resolved, in-situ monitoring of multiple operational and emission parameters in a multi-phase combustion system. The optical detection system operates on the general principle of laser absorption spectroscopy. A molecule has a unique transition between discrete energy states. The unique transition is a function of the particular molecule and a type of molecular bonds the molecule possesses. If the molecule interacts with a photon, for example, which possesses an energy level corresponding to an energy needed to cause the unique transition between discrete energy states, the molecule absorbs the photon and is excited to a higher energy state.

Referring to FIG. 1, the optical detection system includes a tunable diode laser (TDL) 10, an optical network 20, and a detector 30. Although in an exemplary embodiment the optical detection system includes the TDL 10, it is envisioned that any suitable tunable light source may be substituted. The TDL 10 can be frequency tuned to output photons, or light, in a form of a laser beam 12 having the energy level corresponding to the energy level needed to cause the unique transition between discrete energy states of a particular molecule to be detected. The laser beam 12 is then sent to the optical network 20. The optical network 20 directs the laser beam 12 on an optical path through a flow field 100 (see FIG. 7) of the multi-phase combustion system. After the laser beam 12 has passed through the flow field 100, the detector 30 receives light from the laser beam 12 that has not been absorbed by molecules while passing through the flow field 100. An amount of light absorbed, also known as an absorption line strength, can be used to obtain a concentration of the particular molecule to be detected present along the optical path, assuming that Beer-Lambert Law applies. The TDL 10 can also be tuned to measure two or more separate absorption line strengths of the molecule. A ratio of the two absorption line strengths is related to a temperature of the flow field 100.

Many molecules in the multi-phase combustion system are gases of interest to operators of power plants, for example. The concentration of the molecules present may be used to determine if the power plant is meeting regulatory limits, or may be useful in detecting imminent failures in the multi-phase combustion system. Absorption line strengths for many of the molecules in the multi-phase combustion system are detected in the near infrared (IR) range, which is readily covered by the wavelength range of about 650 nm to about 2000 nm. The near IR range is covered by many commercially available TDLs. However, few commercially available TDLs currently offer extremely fast tuning over a wide tuning range with superior accuracy, stability, and repeatability.

In an exemplary embodiment, the TDL 10 is capable of extremely fast tuning (up to about $10^6$ nm/sec) continuously over a range of up to about 80 nm. The TDL 10 operates one or more laser diodes, and can be packaged in a single housing as small as a palm-size device. The TDL 10 has no moving parts and is a robust, all-electronic device. The TDL 10 uses current injection for the extremely fast tuning (up to about $10^6$ nm/sec) continuously over the range of up to about 80 nm. Considering a typical line width of a particular absorption line is on the order of about 0.1 nm or less, it will take about 100 nanoseconds (ns) for the TDL 10 to tune across an entire absorption line.

Figure 2:
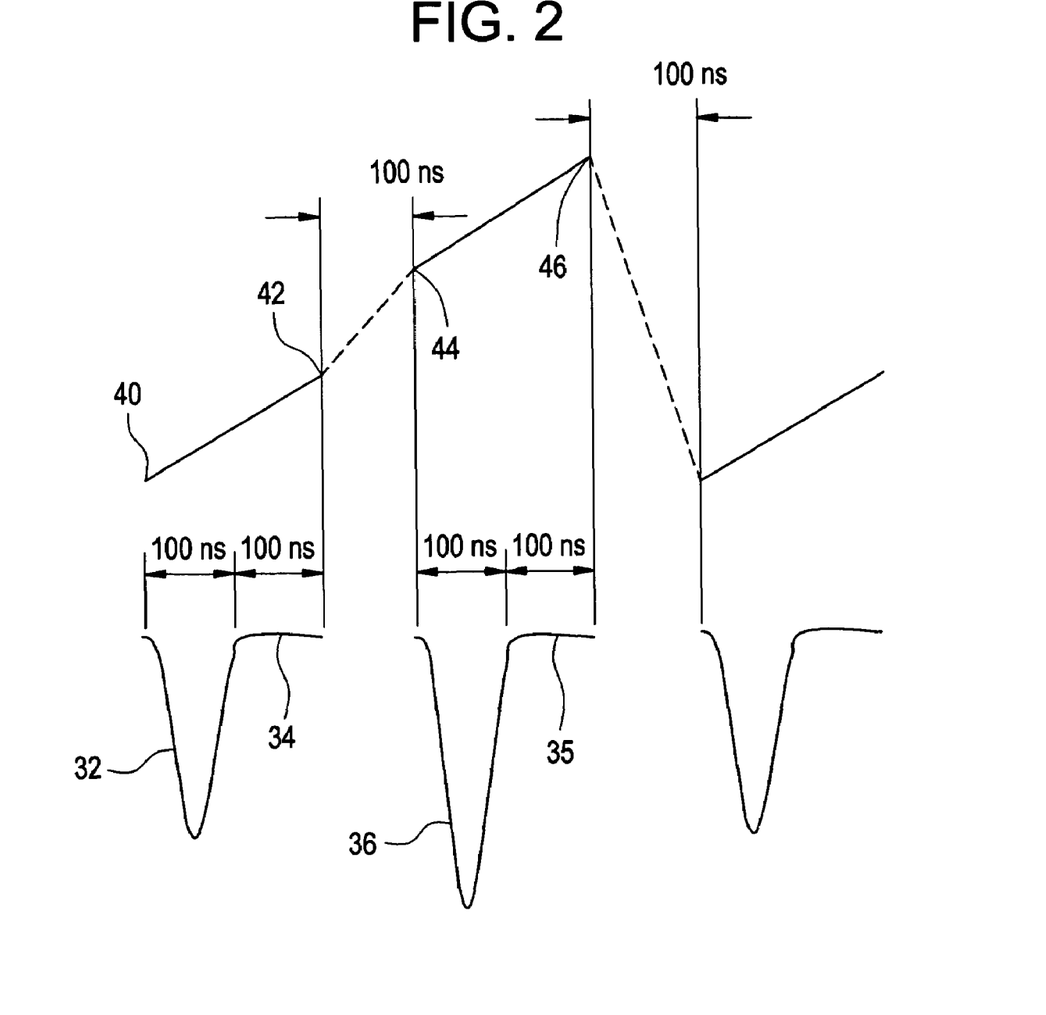
FIG. 2 shows a tuning process for two absorption lines of a particular molecule according to an exemplary embodiment.

FIG. 2 depicts a tuning process for two separate absorption lines of a first particular molecule in accordance with an exemplary embodiment. The TDL 10 uses about 100 ns to scan through a first absorption line 32. The TDL 10 then continues to scan outside the first absorption line 32 for another about 100 ns to scan a first non-absorbing baseline signal 34. The TDL 10 takes about 100 ns to switch (mode hop) to another wavelength and subsequently spends another about 100 ns to scan a second absorption line 36, which is then followed by another about 100 ns of a second non-absorbing baseline signal 35 scanning. The TDL 10 then may switch back to the first absorption line 32 within about 100 ns. The entire tuning cycle for a two-line scan takes a total of about 600 ns, or about 300 ns per line. To measure a temperature of the first particular molecule, at least the first and second absorption lines 32 and 36 should be scanned. Although in this exemplary embodiment, only the first and second absorption lines 32 and 36 of the first particular molecule were scanned, one skilled in the art will recognize that a plurality of particular molecules could be scanned by tuning the TDL 10 for each of the plurality of particular molecules sequentially. Thus, if five lines are scanned, then up to four molecules concentrations and temperature of the flow field 100 can be obtained.

Referring to FIG. 2, the TDL 10 performs a scan by starting at a first wavelength 40 and gradually increases the wavelength through measurement of the first absorption line 32 and the first non-absorbing baseline signal 34 until it reaches a second wavelength 42. From the second wavelength 42, the TDL 10 rapidly switches to a third wavelength 44. The TDL 10 then gradually increases the wavelength through measurement of the second absorption line 36 and the second non-absorbing baseline signal 35 until it reaches a fourth wavelength 46. At the fourth wavelength 46, the TDL 10 again rapidly switches to either the first wavelength 40 or a different wavelength corresponding to a different molecule.

Considering a flow rate inside the flow field 100 of the multi-phase combustion system typically reaches about 20 m/sec and assuming a turbulent intensity of 300% of a mean turbulent intensity, local turbulent velocity reaches about 60 m/sec. Over a period of 600 ns, the maximum movement of the flow is only about 36 μm (0.036 mm). This movement is only about 3.6% or less compared to the diameter of the laser beam 12 which is typically about 1 mm or larger. Thus, from a frame of reference of the laser beam 12 transmitted by the TDL 10, the flow field 100 is practically stagnant or frozen during an entire tuning cycle. Due to rapid tuning characteristics of the TDL 10, errors due to variations in the flow rate of the flow field 100 are negligible. Note, examples of errors introduced through flow variations include 1) particles flowing in and out of the laser beam 12 changing an amount of scattering and extinction, and 2) absorbing species flowing in and out of the laser beam 12 changing an amount of absorption.

A TDL 10 that lacks the tuning speed referred to above increases error associated with measurements, since the flow field 100 no longer appears frozen to the laser beam 12 and flow variations and therefore errors are no longer negligible. Thus, extremely fast tuning speed is crucial to eliminating flow errors in measurements.

Figure 3:
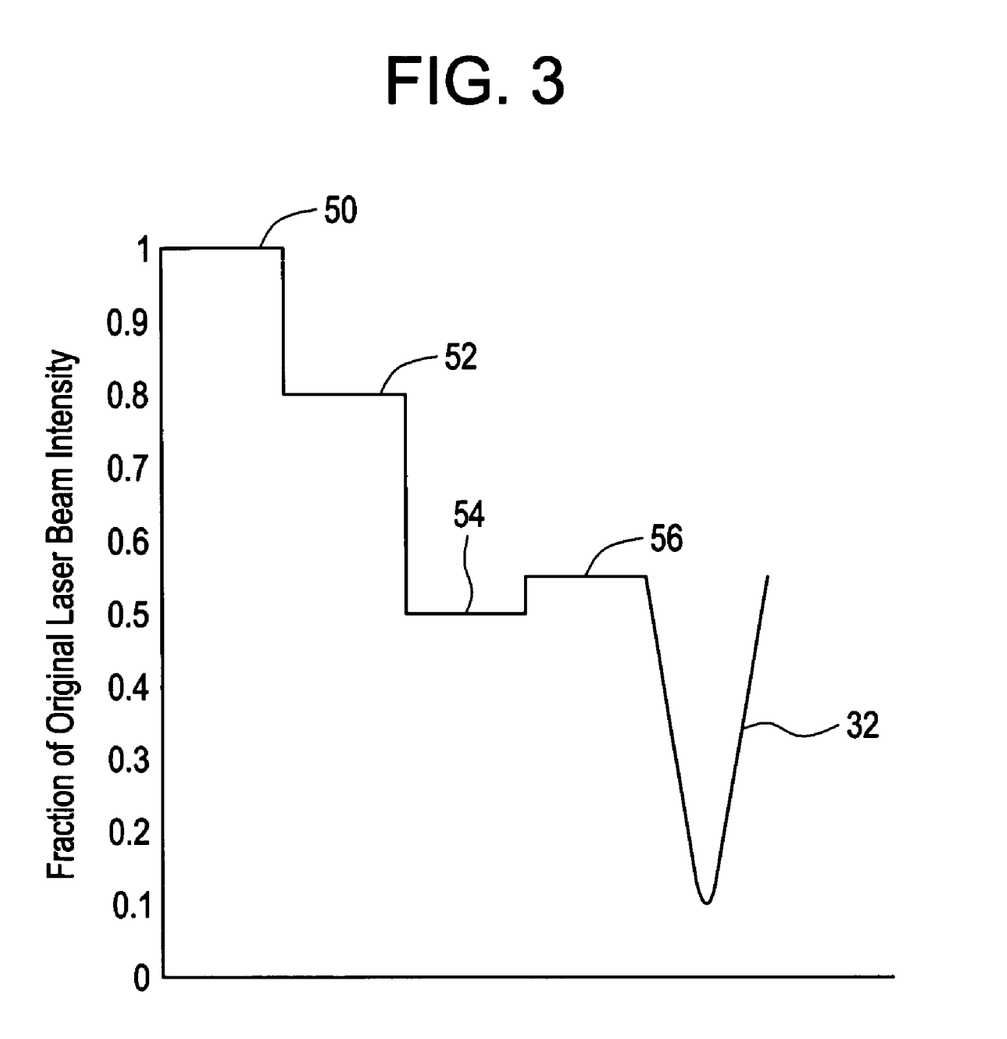
FIG. 3 shows an anatomy of an exemplary absorption signal.

FIG. 3 illustrates a representation of an exemplary absorption signal, for example the first absorption line 32. Numbers on a y-axis are for reference only, representing a fraction of an original laser beam intensity 50. As the laser beam 12 passes through the optical network 20 of FIG. 1 (e.g., fiber optics, a collimating lens, and a dirty optical surface), it loses some fraction of intensity. Post-optics loss intensity 52 is the remaining intensity when losses through the optical network 20 are subtracted. In addition to absorption by any particular molecule, the laser beam 12 still suffers further losses through scattering (by particles with size smaller or comparable to the laser beam 12) and extinction (by particles larger than the laser beam 12) as the laser beam 12 traverses the flow field. Remaining intensity after the losses due to extinction and scattering is post-flow field loss intensity 54. At the detector, a stray light from a source other than the laser beam 12 may also be picked up due to light emissions from the flow field. The stray light however can be minimized using narrow band pass filters. A measured signal intensity, which includes light emissions from the flow field 100 is post-light emissions intensity 56. If the stray light emissions from the flow field 100 are neglected, then the loss due to particulate scattering and extinction are measured with high confidence and the opacity of the flow is derived.

Figure 6:
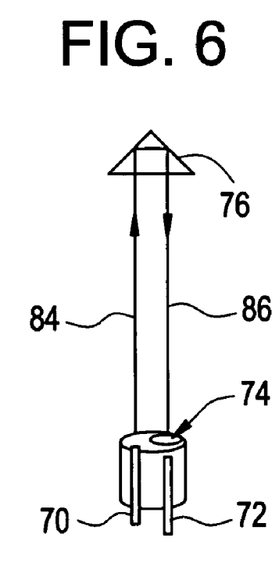
FIG. 6 is an enlarged schematic view of sensing surfaces of the probe in FIG. 5.

In an exemplary embodiment, the optical network 20 includes a fiber optic network having a light transmitter, or a transmitting optical fiber 70, and a light receiver, or a receiving optical fiber 72, to receive the laser beam 12 (see FIG. 6). The simplest method of transmitting and receiving the laser beam 12 is to transmit the laser beam 12 from one side of the flow field 100 and let the laser beam 12 travel across the flow field 100 to be received on the opposite side of the flow field, known as a line of sight measurement. For a large multi-phase combustion system, such as, for example, a large-scale utility boiler, a single pass across the boiler is about 30 to about 40 ft. In high particulate flow regions close to a burner of the boiler, the laser beam 12 may not be able to penetrate through such a great length due to losses through particulate scattering and extinction. To reduce losses due to particulate scattering and extinction, the optical network 20 of FIG. 1 includes a probe 60 (see FIG. 4). The probe 60 allows a shorter optical path through the flow field. The optical path is adjustable in length based on a design of the probe 60. Inserting the probe 60 into high particulate regions of the flow field 100 enables accurate measurement of high particulate regions that is not possible when the laser beam 12 travels across the entire flow field.

Another important aspect associated with using the probe 60 is an ability to generate a localized or high spatial resolution measurement. Compared to the line-of-sight measurement over a long optical path, the probe 60 with the shorter optical path has a much higher spatial resolution. Thus, the probe 60 has an increased ability to pin point a local non-uniformity of a flow parameter. The probe 60 is also retractable allowing it to be inserted into different locations inside the flow field 100 for localized measurements. The probe 60 may be manually or automatically inserted into the flow field 100. In an exemplary embodiment, the probe 60 is inserted into the flow field 100 during measurement and withdrawn from the flow field 100 when not in use.

In an exemplary embodiment, the probe 60 is capable of operation in an environment with temperatures up to about 2500o F. The probe 60 is cooled for high temperature use by passing a cooling fluid through the probe 60, such as, for example, air alone, air and water, etc. An amount of cooling flow required is minimized using any combination of three approaches described below. First, the probe 60 uses a high temperature resistant material to minimize a temperature differential between a hot gas of the flow field 100 and the probe 60. Second, an outer surface of the probe 60 is coated with a thermal barrier coating (TBC) to minimize heat transfer to the probe 60. The TBC also protects metals of the probe 60 from corrosive attack. Third, a diameter of the probe 60 is minimized and hence a surface area for heat transfer is minimized. For example, the diameter of the probe is less than about 2.6 cm.

Figure 4:
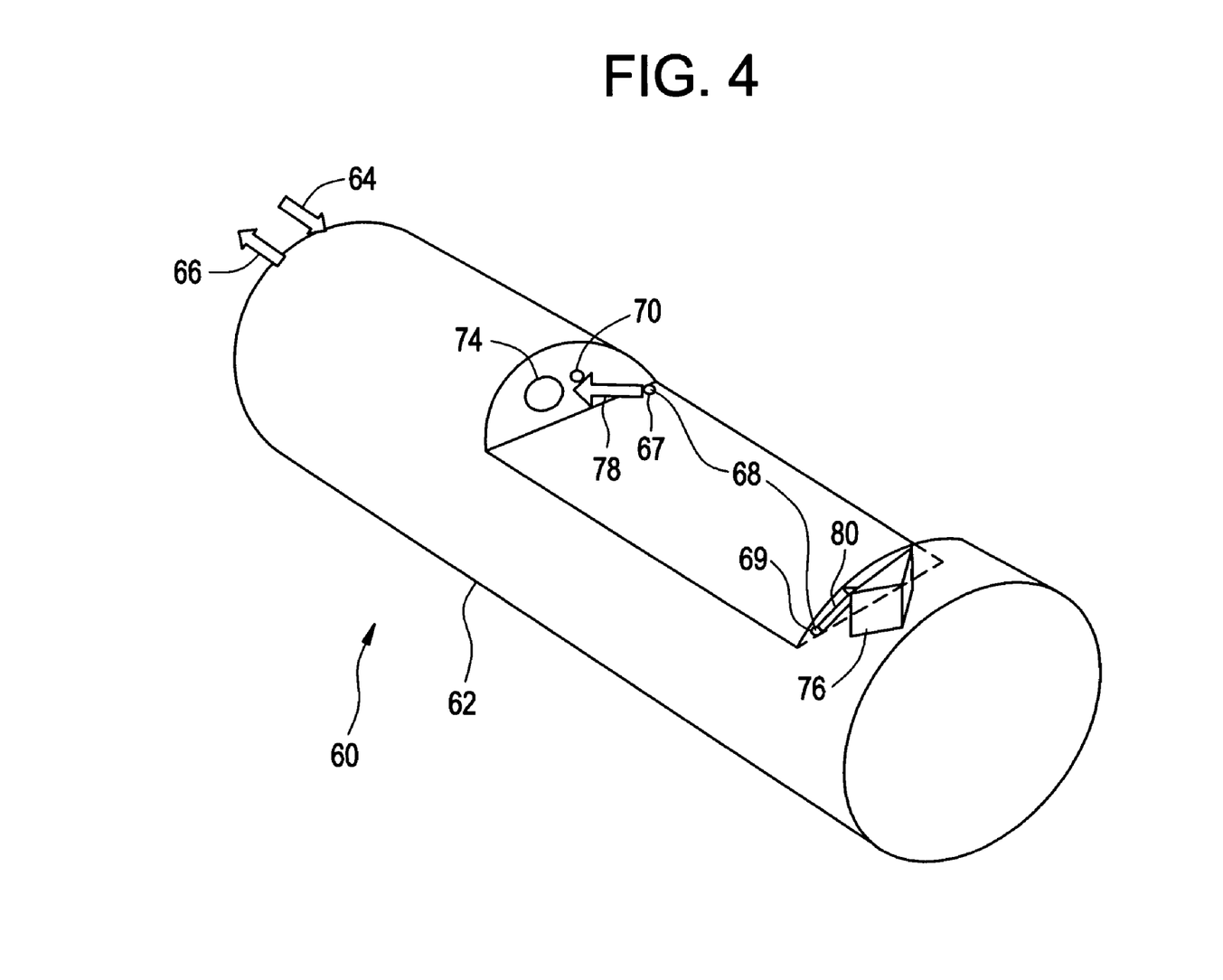
FIG. 4 is a perspective view of a probe according to an exemplary embodiment.

Referring to FIG. 4, in an exemplary embodiment, the probe 60 includes a probe body 62, a cooling and purging fluid inlet 64, a cooling and purging fluid return 66, purge jets 68, the transmitting optical fiber 70, the receiving optical fiber 72 (see FIG. 5), a lens 74, and a prism 76. The probe body 62 includes the high temperature resistant material, the coating with TBC, and the minimized diameter. The cooling and purging fluid inlet 64 allows the cooling fluid to contact the probe body 62 for heat removal. In an exemplary embodiment, the cooling fluid is the same as a purging fluid, although the fluids may be separate. When separate cooling and purging fluids are employed, separate corresponding fluid inlets and outlets are optionally employed. The cooling and purging fluid return 66 provides a return path for the cooling and purging fluids. In an exemplary embodiment, the cooling and purging fluid return 66 is omitted and the cooling and purging fluids are released to the flow field 100. Purge jets 68 direct purge air over the transmitting optical fiber 70, the lens 74, and the prism 76. In this exemplary embodiment, a first purge jet 67 directs a flow of purge fluid substantially perpendicular to the surface of the transmitting optical fiber 70 and the lens 74 in a first direction shown by arrow 78. A second purge jet 69 directs the flow of purge fluid substantially perpendicular to the surface of the prism 76 in a second direction shown by arrow 80. The second direction is substantially opposite to the first direction. While the first and second directions 78 and 80 are opposite in this exemplary embodiment, it is not necessary that the directions 78 and 80 be opposite. The cooling fluid cools the probe body 62 and the purge fluid passes over optical surfaces (e.g., the lens 74, the prism 76, and the transmitting optical fiber 70) of the probe 60 to keep particulates from building up at the optical surfaces. Ideally, a flow rate of the purge fluid is equal to the maximum flow rate of the cooling fluid.

Figure 5:
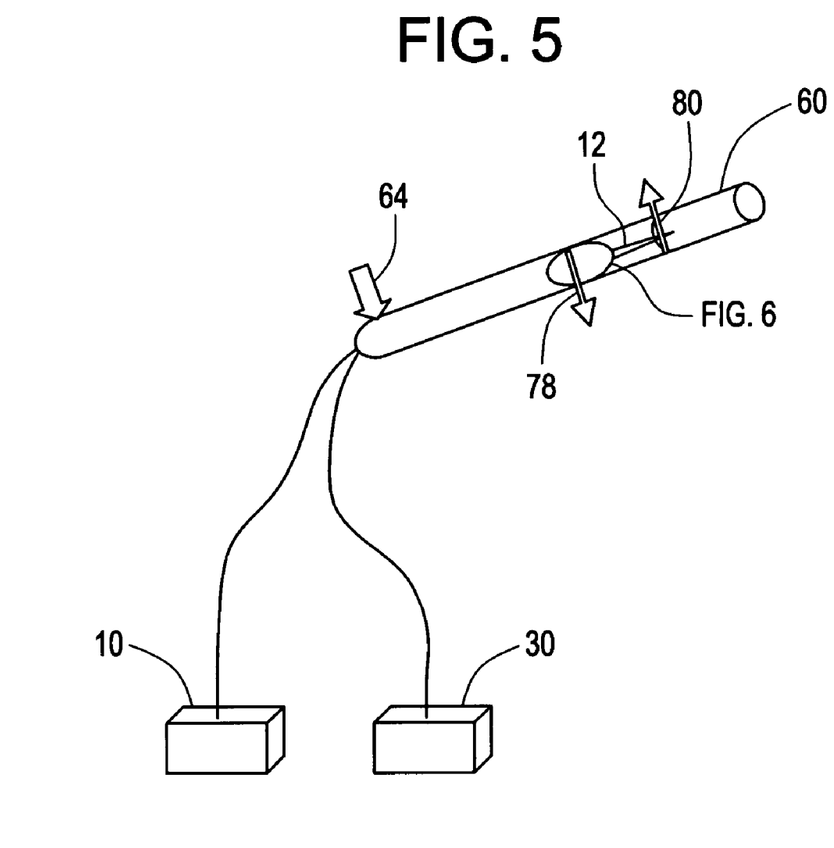
FIG. 5 is a schematic view of an optical detection system wherein an optical network includes the probe of FIG. 4 according to an exemplary embodiment.

FIG. 5 is a schematic view of an optical network 20 including a probe 60 in accordance with an exemplary embodiment. FIG. 6 is an enlarged view of the optical surfaces of the probe 60. Referring to FIGS. 5 and 6, two high temperature gold-coated all silica fiber optic cables capable of operating up to about 1300o F. are fed to the probe 60. One fiber optic cable acts as the transmitting optical fiber 70 and projects the laser beam 12 through the flow field 100 in a first direction 84 and the other fiber optic cable acts as the receiving optical fiber 72. The laser beam 12, after reflecting twice inside a 90o prism 76, travels in a second direction 86 opposite the first direction 84 to the lens 74. The lens 74 is about 5 to about 10 times a diameter of the laser beam 12 and is used to focus the laser beam 12 onto the receiving optical fiber 72. The lens 74 having a larger diameter than the diameter of the laser beam 12 provides beam steering to correct for turbulence in the flow field 100. In an exemplary embodiment, the prism 76 and the lens 74 are made of sapphire for high thermal and chemical resistance, although other suitable materials are also envisioned. Despite the purge jets 68, the optical surfaces of the probe 60 may be coated by particulates causing attenuation of the laser beam 12. However, coating of the optical surfaces has no effect until a detected signal at a peak of absorption approaches a noise level. The non-absorbing baseline signal provides evidence of the coating of the optical surfaces. Thus, the non-absorbing baseline signal 34 is monitored for a downward drift over time. A warning is issued when the downward drift suggests a cleaning of the probe 60.

As discussed above, multiple measurements including the concentration of a plurality of molecules, temperature, and opacity can be performed. Yet other types of measurements can also be integrated. For example, measurements based on collecting light emissions from the flow field 100 are achieved by collecting light using either the transmitting and receiving optical fibers 70 and 72, or by bundling a separate optical fiber to either the transmitting or receiving optical fiber 70 or 72, taking advantage of utilizing a same optic access. Thus in one probe 60, multiple sensors can be packaged for different measurements. The light collected can then be coupled to either a spectrometer or a photodiode and selective band pass filter combination to yield spectrally resolved measurements. Light emissions in a UV range can be used to obtain temperature and fuel-air ratio information. Light emissions in the IR range can be used for pyrometric measurements. Individual spectral lines can also be used to monitor alkali metals. Thus with minimal modification to the optical detection system, but without additional optical access, a whole new category of measurements can be added.

Figure 7:
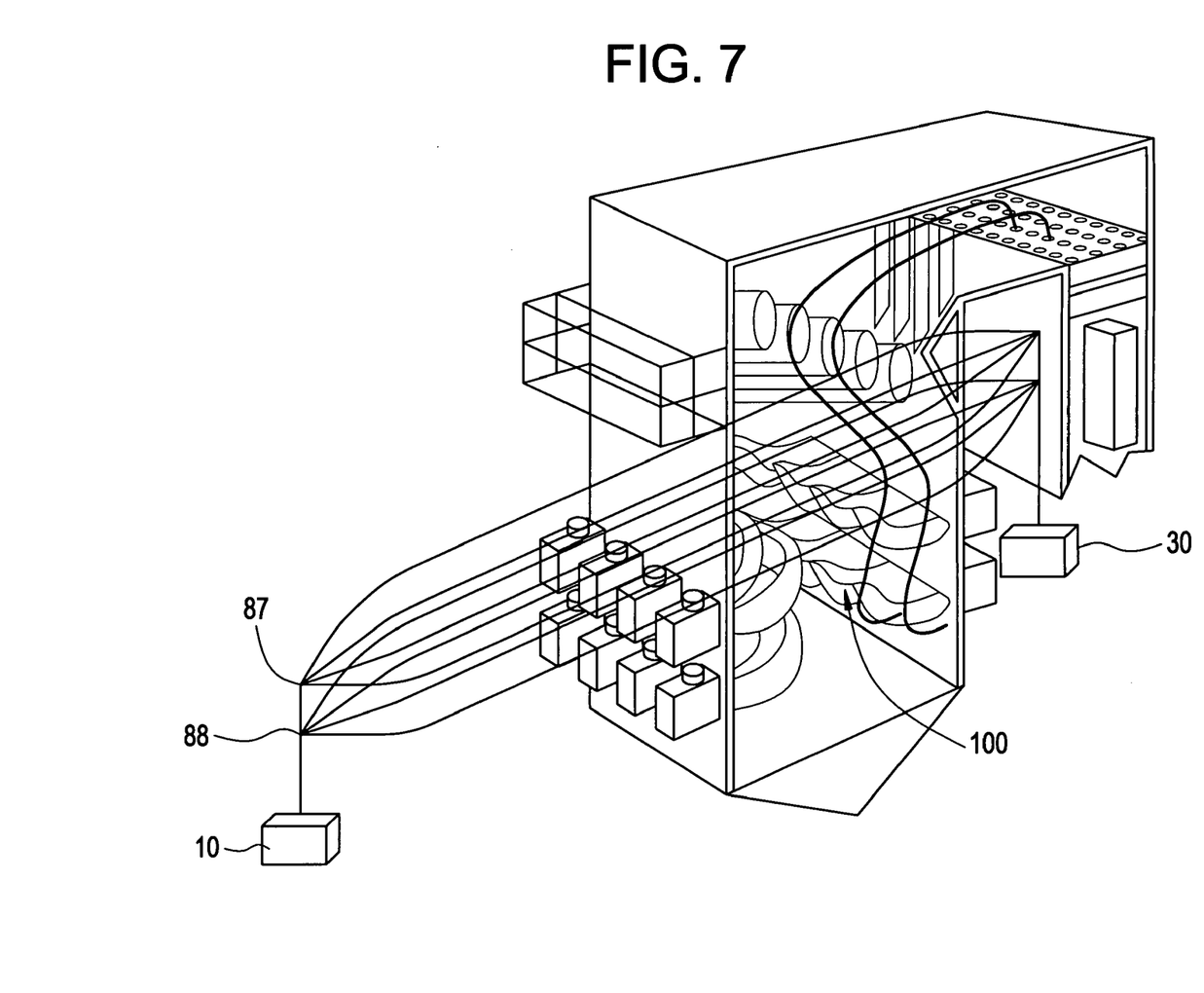
FIG. 7 is a schematic diagram of the optical detection system using a multiple sensor approach to measure a parameter in a flow field according to an exemplary embodiment.

As stated above, the probe 60 is optionally retractable and is adapted to use in harsh flow field 100 environments. Due to properties of the probe 60, a placement of a plurality of probes 60 throughout the flow field 100 (see FIG. 8) is possible. The plurality of probes 60 is configurable to form a grid to yield two dimensional (2-D) or even three dimensional (3-D) information, using a multiple sensor approach. Disposing the plurality of probes 60 such that each probe 60 lies coplanar within the flow field 100 allows a 2-D representation of a parameter measured. Disposing the plurality of probes 60 such that each probe 60 lies non-coplanar throughout the flow field 100 allows a 3-D representation of the parameter measured. The 3-D representation is also achieved where the plurality of probes 60 is disposed such that the probes 60 lie in more than one plane. 2-D and 3-D measurements are also possible in an exemplary embodiment where multiple line-of-sight measurements are performed as shown in FIG. 7. 2-D representation of the parameter measured results by utilizing a first plane of optical paths 87 through the flow field 100. 3-D representation of the parameter measured results by using the first plane of optical paths 87 in combination with a second plane of optical paths 88.

Use of the plurality of probes 60, or multiple line-of-sight measurements requires the use of either multiple TDLs 10 and detectors 30, or multiplexing devices (light switches) to allow a resource sharing of the TDL 10 and the detector 30. FIG. 7 illustrates the optical network 20 for the resource sharing using a configuration of multiple line-of-sight measurements. Use of the plurality of probes 60, or multiple line-of-sight measurements performs a laser tomography of the flow field.

Figure 8:
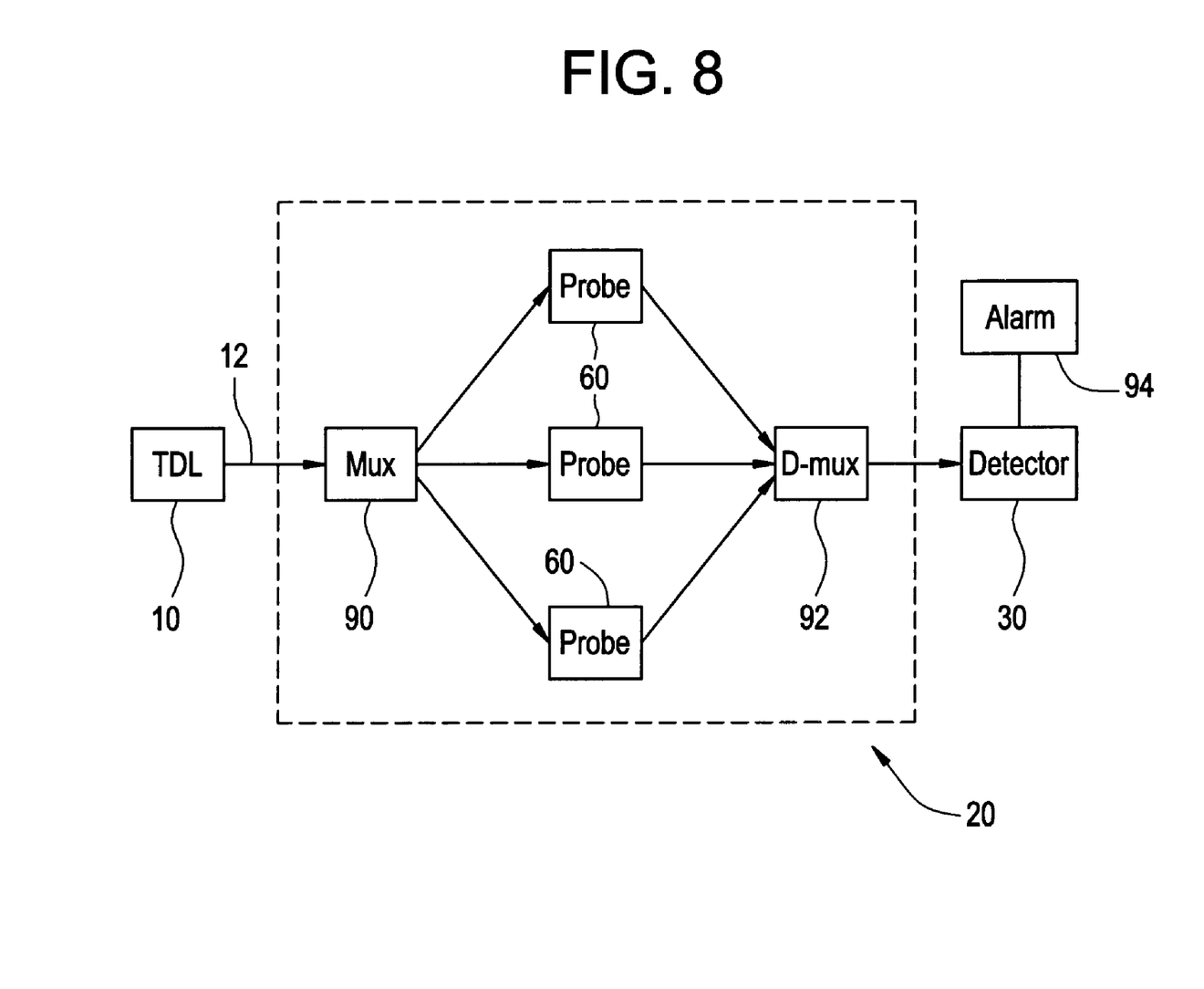
FIG. 8 is a block diagram of the optical detection system using a multiple sensor approach wherein a plurality of probes is included in the optical network according to an exemplary embodiment.

A simple multiple sensor approach comprises only one TDL 10, one detector 30 and the optical network 20 including a multiplexer 90 and a demultiplexer 92 as shown in FIG. 8. The multiplexer 90 multiplexes the laser beam 12 to supply the plurality of probes 60. The demultiplexer 92 demultiplexes the output of each probe 60 of the plurality of probes 60 to allow the use of a single detector 30. In an exemplary embodiment, the detector 30 is equipped with an alarm 94 that issues the warning when the downward drift suggests a cleaning of the probe 60.

In addition, while the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method for in-situ monitoring of an emission product comprising:
    transmitting a light from a first location using a tunable light source;
    tuning said light to a first wavelength corresponding to a first absorption line of the emission product;
    receiving said light at a second location, said light passing along an optical path through the emission product between said first and second locations;
    varying said light from said first wavelength to a second wavelength during a first period;
    measuring said first absorption line and a first non-absorbing baseline signal during said first period;
    switching said light to a third wavelength different from said first and second wavelengths;
    varying said light from said third wavelength to a fourth wavelength over a second period; and
    measuring a second absorption line and a second non-absorbing baseline signal during said second period.

2. The method of claim 1, wherein said switching said light to said third wavelength switches in less than about 100 nsec.

3. The method of claim 1, wherein said measuring said first and second absorption lines further comprises said first and second periods each being about 100 nsec long, said first and second absorption lines are measured during a first half of said first and second periods, respectively, and said first and second non-absorption baseline signals are measured during a second half of said first and second periods, respectively.

4. The method of claim 1, further comprising disposing said first and second locations in a probe.

5. The method of claim 4, wherein said probe includes a 90-degree prism disposed in an optical communication path between said first and second locations for reflecting said light.

6. The method of claim 4, further comprising disposing a plurality of probes in at least one of:
- a coplanar arrangement within a flow field to produce a two dimensional representation of a parameter of the emission product a non-coplanar arrangement within said flow field to produce a three dimensional representation of said parameter of the emission product; and
- in a plurality of planes of said flow field to produce said three dimensional representation of said parameter of the emission product.

7. The method of claim 1, further comprising at least one of:
- calculating a concentration of the emission product using said first absorption line;
- calculating a temperature of the emission product using said first and second absorption lines; and
- calculating an opacity of the emission product.

8. The method of claim 1, further comprising repeating the method of claim 1 using one of a same first wavelength and a different first wavelength corresponding to a first absorption line of a different emission product.

9. A spectrographic sensing system for in-situ monitoring of an emission product comprising:
- a tunable light source capable of tuning a laser beam over a range of about 80 nm at a tuning rate of $10^6$ nm/sec;
- a detector configured to receive said laser beam; and
- an optical network disposed in a flow field, said optical network providing optical communication between said tunable light source and said detector.

10. The system of claim 9, wherein said optical network comprises:
- a transmitter configured to transmit said laser beam from said tunable light source; and
- a receiver configured to receive said laser beam from said tunable light source, said receiver in optical communication with said transmitter via an optical path through said flow field.

11. The system of claim 10, wherein said transmitter and said receiver are disposed in a probe.

12. The system of claim 11, wherein said probe includes a reflector to provide optical communication between said transmitter and said receiver.

13. The system of claim 12, wherein said reflector comprises a 90-degree prism.

14. The system of claim 11, wherein said receiver comprises a lens having about five times to about ten times larger diameter than a diameter of said laser beam.

15. The system of claim 11, wherein said probe is defined by a body comprising at least one of:
- a thermal barrier coating;
- a high temperature resistant material; and
- a diameter of said body being less than about 2.6 cm.

16. The system of claim 12, wherein said probe includes a fluid jet.

17. The system of claim 16, wherein said fluid jet passes a purge fluid over a surface of at least one of:
- said receiver;
- said transmitter; and
- said reflector.

18. The system of claim 11, wherein a cooling fluid cools said probe.

19. The system of claim 10, further comprising a plurality of transmitters and a corresponding plurality of receivers in optical communication via a corresponding plurality of optical paths through said flow field.

20. The system of claim 19, wherein said plurality of transmitters and receivers are disposed in said flow field to produce at least one of:
- coplanar optical paths through said flow field to provide a two dimensional representation of a parameter of the emission product;
- non-coplanar optical paths through said flow field to provide a three dimensional representation of said parameter of the emission product; and
- a plurality of coplanar optical paths through said flow field to provide said three dimensional representation of said parameter of the emission product.

* * * * *